United States Patent
Tolleson et al.

(10) Patent No.: US 6,995,292 B2
(45) Date of Patent: *Feb. 7, 2006

(54) PROCESS FOR REDUCING FLUORIDE IMPURITIES RESULTING FROM USE OF FLUOROPHOSPHITE CATALYSTS

(75) Inventors: Ginette Struck Tolleson, Longview, TX (US); Thomas Allen Puckette, Longview, TX (US)

(73) Assignee: Eastman Chemical Company, Kingsport, TN (US)

(*) Notice: Subject to any disclaimer, the term of this patent is extended or adjusted under 35 U.S.C. 154(b) by 500 days.

This patent is subject to a terminal disclaimer.

(21) Appl. No.: 10/244,297

(22) Filed: Sep. 16, 2002

(65) Prior Publication Data

US 2004/0054211 A1    Mar. 18, 2004

(51) Int. Cl.
    C07C 45/00    (2006.01)
(52) U.S. Cl. ............... 568/429; 568/451; 568/454
(58) Field of Classification Search ......... 568/429, 568/451, 454
    See application file for complete search history.

(56) References Cited

U.S. PATENT DOCUMENTS

| | | | |
|---|---|---|---|
| 3,239,566 A | 3/1966 | Slaugh et al. | |
| 3,284,350 A | 11/1966 | Williamson | |
| 3,527,809 A | 9/1970 | Pruett et al. | |
| 3,959,132 A | 5/1976 | Singh | |
| 4,608,239 A | 8/1986 | Devon | |
| 4,789,753 A | 12/1988 | Billing et al. | |
| 4,912,155 A | 3/1990 | Burton | |
| 5,208,362 A | 5/1993 | Glass et al. | |
| 5,840,647 A | 11/1998 | Puckette et al. | |
| 6,846,960 B2 * | 1/2005 | Tolleson et al. | ............ 568/429 |

FOREIGN PATENT DOCUMENTS

| | | |
|---|---|---|
| WO | WO 01/051441 A | 7/2001 |
| WO | WO 02/098825 | 12/2002 |
| WO | WO 03/061822 | 7/2003 |

OTHER PUBLICATIONS

Riesel et al., *J.Z. Anorg. Allg. Chem.* (1991), pp. 145-150, vol. 603.
Tullock et al., *J. Org. Chem.* (1960), pp. 2016-2019, vol. 25.
White et al., *J. Am. Chem. Soc.* (1970), pp. 7125-7135, vol. 92.
Meyer et al., *Z. Naturforsch, Bi. Chem. Sci.* (1993) pp. 659-671, vol. 48.
U.S. Appl. No. 10/244,264, Tollison et al.
Klender, G. J., *Adv. In Chem. Series*, 249, "Polymer Durability", Ed. R. L. Clough, pp. 397-423.
Lewis, Richard J., *Hawley's Condensed Chemical Dictionary*, 13th Ed. p. 21.
Office Action dated Sep. 3, 2003, from co-pending U.S. Appl. No. 10/244,264 filed on Sep. 16, 2002.

\* cited by examiner

*Primary Examiner*—Sikarl A. Witherspoon
(74) *Attorney, Agent, or Firm*—Michael J. Blake; Bernard J. Graves, Jr.

(57) ABSTRACT

Described is a process for reducing the fluoride content of products prepared in a process utilizing a fluorophosphite-containing transition metal complex catalyst, involving contacting the products with an adsorbent.

18 Claims, No Drawings

PROCESS FOR REDUCING FLUORIDE IMPURITIES RESULTING FROM USE OF FLUOROPHOSPHITE CATALYSTS

FIELD OF THE INVENTION

This invention relates to a process for reducing the amount of fluoride contained in a chemical product. More particularly, this invention relates to a process for reducing the amount of fluoride in a product which has been synthesized using a fluorophosphite-containing catalyst, wherein the resultant products are contacted with an adsorbent for the purpose of reducing the fluoride content of the product.

BACKGROUND OF THE INVENTION

It is known from U.S. Pat. No. 5,840,647 that certain fluorophosphite ligands may be used to form transition metal complexes that serve as catalysts in a wide variety of transition metal catalyzed processes. A particularly suitable process is the hydroformylation or oxo reaction to form aldehydes. It is further known from the above patent that fluorophosphite diester compounds are useful as ligands in catalyst systems for the conversion of olefins to aldehydes. The fluorophosphite ligands can be substituted for, or used in combination with, known phosphite and/or phosphine ligands in a wide variety of catalyst systems using a transition metal as the primary catalyst component. Thus, the catalyst system comprises a combination of one or more transition metals selected from the Group VIII metals and rhenium and one or more fluorophosphite compounds having the general formula

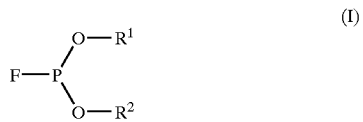

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1. The catalyst systems may be used in a wide variety of transition metal-catalyzed processes such as, for example, hydroformylation, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are especially useful for the hydroformylation of olefins to produce aldehydes and, therefore, are preferred.

When fluorophosphite-containing catalysts are used in reactions to produce chemical products, there is a possibility that the resultant products could contain fluoride as a result of the decomposition of the fluorophosphite ligand transition metal complex. It would therefore be desirable to have a process for reducing the amount of fluoride in a chemical product. It would also be useful to have a process for producing a chemical product using a fluorophosphite-containing catalyst wherein the resultant product, if containing fluoride, has reduced levels of fluoride.

Therefore it is an object of this invention to provide a process for reducing the amount of fluoride in a chemical product. It is also an object of this invention to provide a process for producing a chemical product using a fluorophosphite-containing catalyst wherein the resultant product, if containing fluoride, has reduced levels of fluoride.

SUMMARY OF THE INVENTION

The process of the present invention comprises any transition metal-catalyzed process utilizing a fluorophosphite-containing catalyst wherein the product resulting from the process is contacted with an adsorbent. The adsorbent comprises any material that will adsorb fluoride, and thereby reduce the amount of fluoride in the product of the process.

DETAILED DESCRIPTION OF THE INVENTION

The process of the present invention comprises any transition metal-catalyzed process using a fluorophosphite-containing catalyst wherein the product resulting from the process is contacted with an adsorbent. The adsorbent comprises any material that will adsorb fluoride, and thereby reduce the amount of fluoride in the product of the process.

The process of the present invention is applicable to any transition metal-catalyzed process utilizing a fluorophosphite-containing catalyst. Exemplary of such processes are, preferably, the hydroformylation or oxo reaction to form aldehydes, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are especially useful for the hydroformylation of olefins to produce aldehydes and, therefore, are preferred.

The fluorophosphite-containing catalysts of the present invention are defined in U.S. Pat. No. 5,840,647, which is incorporated herein by reference. More particularly, the fluorophosphite-containing catalyst comprises a combination of one or more transition metals selected from the Group VIII metals and rhenium and one or more fluorophosphite compounds having the general formula

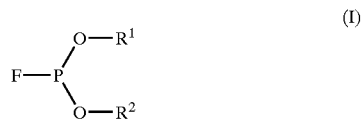

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1.

Fluorophosphite ester compounds having the formula

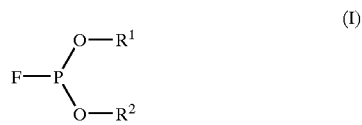

(I)

function as effective ligands when used in combination with transition metals to form catalyst systems for the processes described hereinabove. The hydrocarbyl groups represented by $R^1$ and $R^2$ may be the same or different, separate or combined, and are selected from unsubstituted and substituted alkyl, cycloalkyl and aryl groups containing a total of up to about 40 carbon atoms. The total carbon content of substituents $R^1$ and $R^2$ preferably is in the range of about 2 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. The alkyl and cycloalkyl groups which $R^1$ and/or $R^2$ individually can represent preferably are alkyl of up to about 8 carbon atoms, benzyl, cyclopentyl, cyclohexyl or cycloheptyl.

Examples of the aryl groups which $R^1$ and/or $R^2$ individually can represent include carbocyclic aryl such as phenyl, naphthyl, anthracenyl and substituted derivatives thereof. Examples of the carbocyclic aryl groups which $R^1$ and/or $R^2$ individually can represent the radicals having the formulas

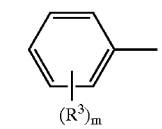
(II)

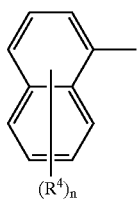
(III)

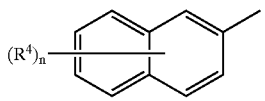
(IV)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. $R^3$ and $R^4$ preferably represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 36 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given hereinbelow as formulas (V), (VI) and (VII).

The divalent groups that $R^1$ and $R^2$ collectively may represent include radicals having the formula

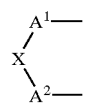

wherein each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula —(CH$_2$)$_y$— wherein y is 2 to 4 or a group having the formula

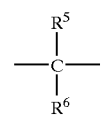

wherein $R^5$ is hydrogen, alkyl or aryl, e.g., the aryl groups illustrated by formulas (II), (III) and (IV), and $R^6$ is hydrogen or alkyl. The total carbon content of the group —C($R^5$)($R^6$)— normally will not exceed 20 and, preferably, is in the range of 1 to 8 carbon atoms. Normally, when $R^1$ and $R^2$ collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals having the formulas:

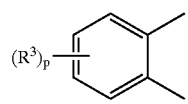
(V)

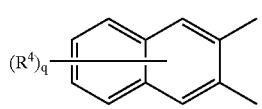
(VI)

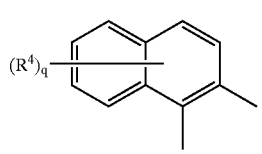
(VII)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent lower alkyl groups, i.e., straight-chain and branched-chain alkyl of up to about 4 carbon atoms, and p and q each represent 0, 1 or 2.

The fluorophosphite esters that are most preferred, e.g., those which exhibit the best stability, are those wherein the fluorophosphite ester oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, it is further preferred that 1 or both of the ring carbon atoms that are in a position ortho to the ring carbon atoms bonded to the fluorophosphite ester oxygen atom are substituted with an alkyl group, especially a branched chain alkyl group such as isopropyl, tert-butyl, tert-octyl and the like. Similarly, when $R^1$ and $R^2$ collectively represent a radical having the formula

the ring carbon atoms of arylene radicals $A^1$ and $A^2$ that are in a position ortho to the ring carbon atoms bonded to the fluorophosphite ester oxygen atom are substituted with an alkyl group, preferably a branched chain alkyl group such as isopropyl, tert-butyl, tert-octyl and the like. The most preferred fluorophosphite esters have the general formula

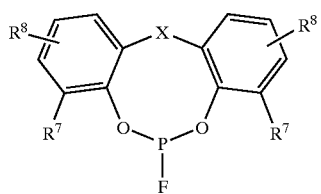

wherein each $R^7$ is alkyl of 3 to 8 carbon atoms; each $R^8$ is hydrogen, alkyl of 1 to 8 carbon atoms or alkoxy of 1 to 8 carbon atoms; and X is (i) a chemical bond directly between ring carbon atoms of each phenylene group to which X is bonded; or (ii) a group having the formula

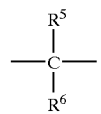

wherein each of $R^5$ and $R^6$ is hydrogen or alkyl of 1 to 8 carbon atoms.

The fluorophosphite esters of formula (I) may be prepared by published procedures or by techniques analogous thereto. See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. The organic moiety of the fluorophosphite compounds, i.e., the residue(s) represented by $R^1$ and $R^2$ can be derived from chiral or optically active compounds. Fluorophosphite ligands derived from chiral glycols or phenols will generate chiral ligands.

The catalyst systems provided by the present invention comprise a combination of one or more transition metals selected from the Group VIII metals and rhenium and one or more of the fluorophosphite compounds described in detail hereinabove. The transition metal may be provided in the form of various metal compounds such as carboxylate salts of the transition metal. Rhodium compounds that may be used as a source of rhodium for the active catalyst include rhodium II or rhodium III salts of carboxylic acids, examples of which include di-rhodium tetraacetate dihydrate, rhodium (II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the fluorophosphite ligands of the present invention. Less desirable rhodium sources are rhodium salts of strong mineral acids such as chlorides, bromides, nitrates, sulfates, phosphates and the like.

The ratio of gram moles fluorophosphite ligand to gram atoms transition metal can vary over a wide range, e.g., gram mole fluorophosphite:gram atom transition metal ratios of about 1:1 to 200:1. For the rhodium-containing catalyst systems the gram mole fluorophosphite:gram atom rhodium ratio preferably is in the range of about 1:1 up to 70:1 with ratios in the range of about 1:1 to 50:1 being particularly preferred.

The adsorbent utilized in the present process is any adsorbing material that can adsorb fluoride from the products produced by the fluorophosphite-containing transition metal complex catalyzed processes, thereby yielding products of lowered fluoride content. The amount of adsorbent to be utilized is any amount that is sufficient to reduce the amount of fluoride contained in the product of the process, as compared to a comparative process operated in the absence of adsorbent.

As herein stated, the adsorbent is any material that adsorbs fluoride from the product of the fluorophosphite-containing transition metal complex catalyzed process. Examples of suitable adsorbents are oxides, carboxylates, hydroxides, bicarbonates, carbonates, phosphates, citrates, borates and/or ascorbates of calcium, sodium, magnesium, aluminum, zinc, silver, lithium, potassium, copper, cadmium, barium, and/or silicon. Examples of carboxylates are those obtained from carboxylic acids containing 1–20 carbon atoms, such as formic, propionic, hexanoic, heptanoic, octanoic, decanoic, dodecanoic, tetradecanoic, hexadecanoic, stearic or eicosanic acids. Also suitable for use as adsorbents are mixed salts such as magnesium aluminum carbonates (also known as talcites and hydrotalcites); molecular sieves; ion exchange resins; membranes, and the like. More preferably, the adsorbent is a calcium salt such as calcium carbonate, calcium sulfate, calcium hydroxide; also preferred is a multi-component material that contains substantial amounts of a calcium salt, such as marble chips, crushed limestone or crushed oyster shells. Most preferred for use as the adsorbent is calcium carbonate. In general, preferred adsorbents have low solubility, for example, less than 100 mg/L (milligrams per liter) in the given organic media. Mixtures of adsorbents can be used in the process.

The adsorbent is used in any form, and in any location in the process, that would allow the objective of the process, to reduce fluoride content of the product, to be achieved. For example, the adsorbent may be used as a powdered adsorbent, or in the form of an adsorbent bed, in which instance a resulting product stream may be circulated through a bed of a suitable solid adsorbent. Alternatively, and preferably, a stream of product is passed through a bed of the adsorbent, under conditions to allow sufficient contact time to reduce the fluoride level of the product. The adsorbent bed can be operated in a plug flow, trickle bed, or in any other manner known to those skilled in the art. The fluoride reduction operation can be achieved at ambient to 500 psig, with no particular advantage attributable to the use of elevated pressure. The temperature of the contacting zone can be varied from 0° C. to 110° C., with a temperature of about 50° C. being preferable. Further, the fluoride reduction bed can be operated in a single pass manner, or as a recycled loop feeding from a vessel. The exact manner of operation depends on the amount of fluoride to be removed, the desired final fluoride level, the dimensions of the bed, and other process variables.

The invention will be more readily understood by reference to the following example. There are, of course, many other forms of this invention which will become obvious to one skilled in the art, once the invention has been fully disclosed, and it will accordingly be recognized that this example is given for the purpose of illustration only, and is not to be construed as limiting the scope of this invention in any way.

EXAMPLE

In the following example fluoride concentrations were determined as follows.

Method for Analyzing Fluoride Concentrations

The method described below is a modification of the measurement method described in the manual for the Orion Fluoride Combination Electrode model #96-09. The method uses a buffer referred to as TISAB II. TISAB stands for Total Ionic Strength Adjustor Buffer and it is used to provide constant background ionic strength, decomplex fluoride, and adjust solution pH.

The concentration of hydrofluoric acid contained in a sample was determined by shaking the sample with an equal amount of TISAB II buffer (Orion #940909, recommended buffer for use with a fluoride selective electrode) and separating out the buffer portion. An equal amount of distilled water is added to the buffer portion and the fluoride concentration is measured with an Orion (#96-09) fluoride ion selective electrode that is attached to a Metrohm 751 GPD Titrino titrator. The measurement is in millivolts and this is converted into ppm by using a calibration chart.

The following example shows a hydroformylation process using a fluorophosphite-containing transition metal catalyst to produce butyraldehydes. The process is carried out in a vapor take-off reactor consisting of a vertically arranged stainless steel pipe having a 2.5 cm inside diameter and a length of 1.2 meters. The reactor has a filter element near the bottom of the reactor for the inlet of gaseous reactants. The reactor contains a thermowell which is arranged axially with the reactor in its center for accurate measurement of the temperature of the hydroformylation reaction mixture. The bottom of the reactor has a high pressure tubing connection that is connected to a cross. One of the connections to the cross permits the addition of non-gaseous reactants such as octene-1 or make-up solvent, another leads to the high-pressure connection of a differential pressure (D/P) cell that is used to measure catalyst level in the reactor and the bottom connection is used for draining the catalyst solution at the end of the run.

In the hydroformylation of propylene in a vapor take-off mode of operation, the hydroformylation reaction mixture or solution containing the catalyst is sparged under pressure with the incoming reactants of propylene, hydrogen and carbon monoxide as well as any inert feed such as nitrogen. As butyraldehyde is formed in the catalyst solution, the butyraldehyde and unreacted reactant gases are removed as a vapor from the top of the reactor by a side-port. The vapor removed is chilled in a high pressure separator where the butyraldehyde product is condensed along with some of the unreacted propylene. The uncondensed gases are let down to atmospheric pressure via the pressure control valve. These gases pass through a series of dry-ice traps where any other aldehyde product is collected. The product from the high pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed to the reactor via twin cylinder manifolds and high pressure regulators. The hydrogen passes through a commercially available Deoxo® (registered trademark of Engelhard Inc.) catalyst bed to remove any oxygen contamination and through a flow controller D/P cell and control valve. The carbon monoxide passes through a similar Deoxo® bed heated to 125° C., an iron carbonyl removal bed (as disclosed in U.S. Pat. No. 4,608,239). Nitrogen can be added to the feed mixture as an inert gas. Nitrogen, when added, is metered and then mixed with the hydrogen feed prior to the hydrogen Deoxo® bed. Propylene is fed to the reactor from feed tanks that are pressurized with hydrogen. The propylene feed rate is controlled by a liquid mass flow meter. All gases and propylene are passed through a preheater to insure vaporization of the liquid propylene.

Example

A catalyst solution was prepared under nitrogen using a charge of 0.0375 g rhodium dicarbonyl acetonylacetate, (also known as rhodium dicarbonyl acac, 15 mg Rh), 2.12 g of 2,2'-ethylidene bis(4,6-di-t-butyl-phenyl)fluorophosphite (4.37 mmoles, [L]/[Rh]=30), and 190 ml of dioctylphthalate. The catalyst solution was charged to the reactor under an argon blanket and the reactor was sealed. The reactor was pressurized to 260 psig (18.9 Bar) with hydrogen, carbon monoxide, and nitrogen and heated to 115° C. Propylene feed was then started and the flows were adjusted to the following reported as liters/min at standard temperature and pressure (STP): hydrogen=3.70 l/min STP; carbon monoxide=3.70 l/min STP; nitrogen=1.12 l/min STP; and propylene=2.08 l/min STP. This is equivalent to having the following partial pressures in the feed to the reactor reported as pounds per square inch atmospheric (psia): hydrogen=96 psia (6.6 Bar); carbon monoxide=96 psia (6.6 Bar); nitrogen=29 psia (2.0 Bar); and propylene=54 psia (3.7 Bar).

The reaction was carried out under the above flows for 53 hours. The butyraldehyde production rate averaged 60.86 g/hour for a catalyst activity of 4.06 kilograms butyraldehyde/gram of rhodium-hour. A total of 2.96 liters of butyraldehyde was produced. The ratio of normal isobutyraldehyde product to iso-butyraldehyde product (n:iso) was 3.38/1. The average fluoride concentration in parts per million (ppm) for the aldehyde produced was 0.21 ppm.

The butyraldehyde product, having a fluoride level of 118 mv (0.21 ppm), was poured onto a dry column of marble (Fisher) which weighed 103.6 g in a 12×1 inch (30×2.2 cm) Pyrex tube. The fluoride measurement for a 10 ml sample of aldehyde collected was 174 mv (0.0018 ppm).

The above clearly shows that contacting a fluoride containing product, which was produced in a fluorophosphite-containing transition metal catalyzed process, with an adsorbent results in a decrease of the fluoride content of the product.

While this invention has been described with respect to particular embodiments thereof, it is apparent that numerous other modifications of the invention will be obvious to those skilled in the art. The appended claims and this invention generally should be construed to cover all such obvious forms and modifications which are within the true spirit and scope of the present invention.

We claim:

1. A method for reducing the fluoride content in a product of a chemical process, wherein said chemical process is selected from the group consisting of hydroformylation, hydrogenation, isomerization, hydrocyanation, hydrosilation, carbonylations, oxidations, acetoxylations, epoxidations, hydroamination, dihydroxylation, cyclopropanation, telomerizations, carbon hydrogen bond activation, olefin metathesis, olefin dimerizations, oligomerizations, olefin polymerizations, olefin-carbon monoxide copolymerizations, butadiene dimerization and oligomerization, butadiene polymerization, Heck reaction and arene coupling reaction, wherein said chemical process comprises reacting a reactant mixture in the presence of a catalyst comprising one or more transition metals selected from the group consisting of Group VIII metals and rhenium, and one or more fluorophosphite compounds having the general formula:

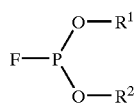  (I)

wherein $R^1$ and $R^2$ are hydrocarbyl radicals which contain a total of up to about 40 carbon atoms and wherein the ratio of gram moles fluorophosphite ligand to gram atoms transition metal is at least 1:1, to produce a product containing fluoride, said method comprising contacting said product with an adsorbent to reduce the fluoride content in said product, wherein said adsorbent is selected from the group consisting of (a) oxides, carboxylates, hydroxides, bicarbonates, carbonates, phosphates, citrates, borates or ascorbates and mixtures thereof, and (b) calcium, sodium, magnesium, aluminum, zinc, silver, lithium, potassium, copper, cadmium, barium, silicon, talcites, hydrotalcites, molecular sieves, ion exchange resins, or mixtures thereof.

2. The method according to claim 1 wherein said chemical process is hydroformylation of an olefin to produce an aldehyde.

3. The method according to claim 1 wherein said adsorbent has a solubility of less than 100 mg/L in said product.

4. The process according to claim 1 wherein said adsorbent comprises a calcium containing compound.

5. The process according to claim 1 wherein said adsorbent comprises calcium carbonate.

6. The process according to claim 1 wherein said adsorbent is selected from the group consisting of calcium carbonate, calcium sulfate, and calcium hydroxide.

7. The process according to claim 1 wherein said adsorbent is selected from the group consisting of marble, crushed oyster shells, and limestone.

8. The process according to claim 1 wherein said adsorbent is selected from the group consisting of carboxylates containing 1–20 carbon atoms of calcium, sodium, magnesium, aluminum, zinc, silver, lithium, potassium, copper, cadmium, barium, silicon, and mixtures thereof.

9. The process according to claim 1 wherein said adsorbent is selected from the group consisting of magnesium aluminum carbonates, molecular sieves, ion exchange resins, and membranes.

10. A method for reducing the fluoride content in an aldehyde product of a hydroformylation process, wherein said process comprises reacting an alkenyl olefin in a reactant mixture in the presence of a catalyst comprising one or more transition metals selected from the group consisting of Group VIII metals and rhenium, and one or more fluorophosphite compounds having the general formula

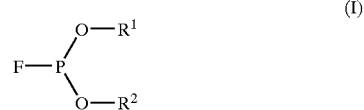  (I)

wherein $R^1$ and $R^2$ are hydrocarbyl radicals which contain a total of up to about 40 carbon atoms and wherein the ratio of gram moles fluorophosphite ligand to gram atoms transition metal is at least 1:1, to produce an aldehyde product containing fluoride, said method comprising contacting said product with an adsorbent to reduce the fluoride content in said product, wherein said adsorbent is selected from the group consisting of: (a) oxides, carboxylates, hydroxides, bicarbonates, carbonates, phosphates, citrates, borates and ascorbates or mixtures thereof and (b) calcium, sodium, magnesium, aluminum, zinc, silver, lithium, potassium, copper cadmium, barium, silicon, talcites, hydrotalcites, molecular sieves, ion exchange resins, or mixtures thereof.

11. The method according to claim 10 wherein said adsorbent has a solubility of less than 100 mg/L in said product.

12. The process according to claim 10 wherein said adsorbent comprises a calcium containing compound.

13. The process according to claim 10 wherein said adsorbent comprises calcium carbonate and said product includes butyraldehyde.

14. The process according to claim 10 wherein said adsorbent is selected from the group consisting of calcium carbonate, calcium sulfate, and calcium hydroxide.

15. The process according to claim 10 wherein said adsorbent is selected from the group consisting of marble, crushed oyster shells, and limestone.

16. The process according to claim 10 wherein said adsorbent is selected from the group consisting of carboxylates containing 1–20 carbon atoms of calcium, sodium, magnesium, aluminum, zinc, silver, lithium, potassium, copper, cadmium, barium, silicon, and mixtures thereof.

17. The process according to claim 10 wherein said adsorbent is selected from the group consisting of magnesium aluminum carbonates, molecular sieves, ion exchange resins, and membranes.

18. The process according to claim 10 wherein said aldehyde product is a mixture of isobutyraldehyde and normal butyraldehyde.

* * * * *